(12) United States Patent
Isola et al.

(10) Patent No.: US 9,393,442 B2
(45) Date of Patent: Jul. 19, 2016

(54) DEVICE FOR DETERMINING ILLUMINATION DISTRIBUTIONS FOR IMRT

(71) Applicant: KONINKLIJKE PHILIPS N.V., Eindhoven (NL)

(72) Inventors: Alfonso Agatino Isola, Eindhoven (NL); Christoph Neukirchen, Aachen (DE); Juergen Weese, Norderstedt (DE); Matthieu Frédéric Bal, Cadier en Keer (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/891,074

(22) PCT Filed: May 14, 2014

(86) PCT No.: PCT/EP2014/059807
§ 371 (c)(1),
(2) Date: Nov. 13, 2015

(87) PCT Pub. No.: WO2014/191204
PCT Pub. Date: Dec. 4, 2014

(65) Prior Publication Data
US 2016/0082287 A1    Mar. 24, 2016

(30) Foreign Application Priority Data

May 29, 2013    (EP) .................................... 13169709

(51) Int. Cl.
*A61N 5/10* (2006.01)
(52) U.S. Cl.
CPC ............ *A61N 5/1036* (2013.01); *A61N 5/1045* (2013.01); *A61N 5/1047* (2013.01); *A61N 2005/1074* (2013.01)

(58) Field of Classification Search
CPC ....... A61N 5/10; A61N 5/103; A61N 5/1031; A61N 5/1045; G21K 1/02; G21K 1/04; G21K 1/046
USPC ..................... 378/65, 147, 150, 151
See application file for complete search history.

(56) References Cited

U.S. PATENT DOCUMENTS

| 6,240,161 B1 | 5/2001 | Siochi |
|---|---|---|
| 2011/0006215 A1 | 1/2011 | Van Heteren et al. |

(Continued)

OTHER PUBLICATIONS

Hadrien Cambazard et al: "A shortest path-based approach to the multileaf collimator sequencing problem", Discrete Applied Mathematics, Elsevier Science, Amsterdam, NL, vol. 160, No. 1, Sep. 2, 2011, pp. 81-99, XP028336352.

(Continued)

*Primary Examiner* — Jurie Yun

(57) ABSTRACT

The invention relates to a device for determining illumination distributions (18) for IMRT. A layered graph structure is used, which considers which extensions of an illumination distribution along a respective line and thus which illumination distributions are realizable, for determining extensions for the illumination distributions. Moreover, second weights defining fluences of the illumination distributions are determined such that a deviation between a provided fluence map and a fluence map formed by a combination of illumination distributions, which are defined by the respective determined extensions and the respective second weight, is minimized. This determination procedure leads to illumination distributions, which very well correspond to the provided fluence map and which are automatically realizable by the radiation device. This leads to an improved IMRT, wherein a post-processing of the determined illumination distributions for ensuring that the determined illumination distributions are really realizable is not necessarily required.

13 Claims, 7 Drawing Sheets

(56) References Cited

U.S. PATENT DOCUMENTS

2011/0091015 A1    4/2011    Yu et al.
2012/0219356 A1    8/2012    Garland et al.
2013/0077751 A1    3/2013    Gunawardena et al.

OTHER PUBLICATIONS

Zhang, et al., "Fluence Map Optimization in IMRT Cancer Treatment Planning and Geometric Approach", Jul. 2004.

Zhang, et al., "A Geometric Approach to Fluence Map Optimization in IMRT Cancer Treatment Planning", Jul. 2004.

Antje Kiesel, "A Function Approximation Approach to the Segmentation Step in IMRT Planning", Dec. 1, 2009, Springer-Verlag 2009.

C. Cameron, "Sweeping-Window arc Theray: an Implementation of rotational IMRT with Automatic Beam-Weight Calculation", Sep. 7, 2005.

Kamath, et al., "Leaf Sequencing Algorithms for Segmented Multileaf Collimation", Phys Med Biol. Feb. 7, 2003.

H.E. Romeijn et al., "A column generation approach to radiation therapy treatment planning using aperture modulation", SIAM J. OPTIM. (2005) vol. 15, No. 3, pp. 838-862.

D. Pflugfelder et al., "A comparison of three optimization algorithms for intensity modulated radiation therapy", Z. Med. Phys. (2008) vol. 18, No. 2, pp. 111-119.

DEVICE FOR DETERMINING ILLUMINATION DISTRIBUTIONS FOR IMRT

CROSS REFERENCE TO RELATED APPLICATIONS

This application is a national filing of PCT application Serial No. PCT/EP2014/059807, filed May 14, 2014, published as WO 2014/191204A1 on Dec. 4, 2014, which claims the benefit of European Application Number 13169709.6 filed May 29, 2013, which is incorporated herein by reference.

FIELD OF THE INVENTION

The invention relates to a device, a method and a computer program for determining illumination distributions to be directed to a target region for performing intensity modulated radiation therapy (IMRT). The invention relates further to an apparatus for performing the IMRT.

BACKGROUND OF THE INVENTION

In IMRT a target region like a tumor region is illuminated from different directions by using different illumination distributions, wherein these illumination distributions are adapted such that, after the target region has been illuminated by the different illumination distributions in the different directions, the target region has received the most radiation dose, whereas the surrounding of the target region has received a radiation dose being as small as possible. The illumination distributions are generally determined in at least two steps. In a first step for each illumination direction a fluence map is calculated under radiation dose constraints, which substantially defines which region should receive which radiation dose, and in a second step for each illumination direction the respective fluence map is transformed into a sequence of illumination distributions realizable by a radiation device used for performing the IMRT. This transformation of the calculated fluence map to the sequence of realizable illumination distributions modifies the radiation doses, which will finally be received by the different regions, and therefore leads to a reduced quality of the IMRT.

SUMMARY OF THE INVENTION

It is an object of the present invention to provide a device, a method and a computer program for determining illumination distributions to be directed to a target region for performing IMRT, which allow for an IMRT having an improved quality. It is a further object of the present invention to provide an apparatus for performing the IMRT.

In a first aspect of the present invention a device for determining illumination distributions to be directed to a target region for performing IMRT is presented, wherein the device comprises:
 a fluence map providing unit for providing a fluence map,
 a layered graph structure providing unit for providing a layered graph structure, wherein the layered graph structure comprises layers with nodes, wherein the nodes of a layer represent realizable extensions of an illumination distribution along a line, which are realizable by a radiation device, wherein the nodes of different layers represent realizable extensions of an illumination distribution along different parallel lines and wherein nodes of adjacent layers are connected by graph edges, to which first weights and regularization values are assigned, wherein the regularization values depend on deviations between the extensions of the illumination distributions represented by the nodes connected by the respective graph edges,
 an extensions determination unit for determining extensions of an illumination distribution along the parallel lines for several illumination distributions, wherein the extensions determination unit is adapted to determine the extensions for an illumination distribution by determining a sequence of nodes connected by the graph edges through the layered graph structure, which optimizes a cost function that depends on a combination of the first weights and the regularization values assigned to the graph edges connecting the nodes of the sequence, thereby determining a contour of the illumination distribution,
 a second weights determination unit for determining second weights defining the fluences of the illumination distributions, for which the extensions have been determined, such that a deviation between the provided fluence map and a combination of the illumination distributions having the determined extensions and the fluences defined by the second weights is minimized.

By using the layered graph structure, which considers which extensions of an illumination distribution along a respective line and thus which illumination distributions are realizable, for determining sequences of nodes and, thus, of extensions for the illumination distributions and by determining the second weights for the illumination distributions such that a deviation between the provided fluence map and a fluence map formed by a combination of illumination distributions, which are defined by the respective determined extensions and the respective second weight, is minimized, the determined illumination distributions correspond to the provided fluence map very well, wherein these illumination distributions are automatically realizable by the radiation device. This leads to an improved IMRT, if the IMRT is performed in accordance with these determined illumination distributions.

An illumination distribution, which may also be regarded as being a segment, can be defined by its extensions in a certain direction, for instance, in a row direction or a column direction, i.e. it can be defined by the shape of its opening, and by the fluence of the illumination along this opening. Preferentially, the fluence is constant along the opening of an illumination distribution, i.e. of a segment. The constant fluence of the respective opening of the respective segment is defined by the second weight determined for the respective illumination distribution. The fluences may be defined by the respective beam-on times and the intensity of the beam.

The fluence map providing unit can be a storing unit, in which a desired ideal fluence map is stored already, or it can be a receiving unit for receiving the fluence map via a wired or wireless data connection and for providing the received fluence map. The fluence map providing unit can also be a calculation unit like a processor for calculating the ideal desired fluence map by using known fluence map calculation algorithms, which determine a fluence map based on a desired radiation dose distribution within a living being like a person or an animal.

The target region is preferentially a region to be treated within a living being. For instance, the target region can be a tumor region within a person. The illumination distributions and the fluence map are preferentially two-dimensional fluence distributions in a plane being substantially perpendicular to the respective illumination direction. The cost function preferentially depends on the sum of all first weights traversed along the sequence of nodes.

It is preferred that the radiation device comprises a combination of a radiation source and a multileaf collimator, wherein the lines, along which the extensions of the illumination distributions are defined, are aligned along the leafs of the multileaf collimator and wherein realizable positions of the leafs of the multileaf collimator define the realizable extensions of the illumination distribution along the respective line. By using a multileaf collimator, arbitrary illumination distributions, in particular, arbitrary extensions of the illumination distributions along the lines, can be provided technically relatively easily and very accurately, which can allow for a further improvement of the IMRT.

It is preferred that the layered graph structure providing unit is adapted to determine a deviation function being indicative of a deviation between the provided fluence map and the combination of illumination distributions having the determined extensions and the fluences defined by the second weights and to determine the first weights depending on the deviation function. It is further preferred that the layered graph structure providing unit is adapted to determine the first weights depending on gradients of the deviation function. Preferentially, the first weights are determined depending on the gradients of the deviation function with respect to pixels of the illumination distributions, i.e. with respect to elements of the respective extensions. In particular, the layered graph structure providing unit can be adapted to determine a first weight for a graph edge depending on the gradients for the extensions represented by the nodes connected by the graph edge. Preferentially, a first weight for a graph edge is determined depending on the gradients for the extensions represented by the nodes connected by the graph edge at all their pixel locations, i.e., for example, for all combinations of the elements of the respective extensions. For instance, the layered graph structure providing unit can be adapted to determine a first weight for a graph edge depending on the sum of the gradients for the extensions represented by the nodes connected by the graph edge at all pixel locations. Determining the first weights in this way can further improve the quality of performing the IMRT.

The deviation function is preferentially indicative of the sum of squared differences between the provided fluence map and the combination of illumination distributions having the determined extensions and the fluences defined by the second weights.

The layered graph structure providing unit may be adapted to assign an infinite value as a first weight to a graph edge for indicating an impossible transfer from one of the nodes connected by the graph edge to another of the nodes connected by the graph edge, if the combination of extensions of the illumination distribution represented by these nodes is not realizable by the radiation device. For instance, an infinite value can be assigned as first weight to the respective graph edge.

Regularization values are assigned to the graph edges. The regularization values depend on deviations between the extensions of the illumination distributions represented by the nodes connected by the respective graph edges. The regularization can be used, for instance, to enforce smooth opening contours and/or a larger opening area, which can lead to a further improved quality of the IMRT.

In an embodiment the layered graph structure providing unit and the extensions determination unit are adapted such that, after the extensions determination unit has determined extensions of an illumination distribution, a) nodes of the layered graph structure are selected based on a selection criterion which depends on the determined extensions, b) regularization values are assigned to the graph edges, and c) the extensions of the illumination distribution are determined again, wherein only the selected nodes are considered. In particular, the regularization values are assigned to the graph edges only, which correspond to the selected nodes. Since the nodes are selected based on a selection criterion which depends on the determined extensions, the nodes may be selected such that only nodes are selected, which will likely not increase the deviation between the provided fluence map and the combination of all illumination distributions having the determined extensions and the fluences defined by the second weights. The nodes can therefore be selected such that determining the extensions of the illumination distribution again, wherein only the selected nodes are considered, does not likely lead to a solution with reduced quality. Moreover, since in this further determination of the extensions of the illumination distribution, which only considers the selected nodes, regularization values assigned to the graph edges are used in addition to the first weights, regularized extensions of the illumination distribution can be determined with reduced computational efforts.

In a preferred embodiment the layered graph structure providing unit, the extensions determination unit and the second weights determination unit are adapted such that the provision of the layered graph structure, the determination of the extensions and the determination of the second weights is repeatedly performed. In particular, the layered graph structure providing unit may be adapted to repeatedly provide the layered graph structure by repeatedly determining the first weights. Thus, the illumination distributions can be determined in an iterative process, until an abort criterion is fulfilled, for instance, until a predefined number of iterations or a predefined deviation threshold between the provided fluence map and the combination of the illumination distributions forming a real fluence map has been reached.

In a further aspect of the present invention an apparatus for performing IMRT is presented, wherein the apparatus comprises:

a radiation device for providing illumination distributions to be directed to a target region, a device for determining illumination distributions realizable by the radiation device and to be directed to the target region for performing intensity modulated radiation therapy as defined in claim 1, and a control unit for controlling the radiation device in accordance with the determined illumination distributions.

In a further aspect of the present invention a method for determining illumination distributions to be directed to a target region for performing IMRT is presented, wherein the method comprises:

providing a fluence map by a fluence map providing unit, providing a layered graph structure by a layered graph structure providing unit, wherein the layered graph structure comprises layers with nodes, wherein the nodes of a layer represent realizable extensions of an illumination distribution along a line, which are realizable by a radiation device, wherein the nodes of different layers represent realizable extensions of an illumination distribution along different parallel lines and wherein nodes of adjacent layers are connected by graph edges, to which first weights $e_r$ and regularization values are assigned, wherein the regularization values depend on deviations between the extensions of the illumination distributions represented by the nodes connected by the respective graph edges, determining extensions of an illumination distribution along the parallel lines for several illumination distributions by an extensions determination unit, wherein the extensions are determined for an illumination distribution by determining a sequence of nodes connected by the graph edges through the layered graph structure, which optimizes a cost function that depends on a combination of the first weights $e_r$ and the regularization values assigned to the graph edges connecting the nodes of the sequence, thereby determining a contour of the illumination distribution, determining second weights defining the fluences of the illumination distributions, for which the extensions have been determined, by a second weights determination unit such that a deviation between the provided fluence map and a combination of the illumination distributions having the determined extensions and the fluences defined by the second weights is minimized.

In a further aspect of the present invention a computer program for determining illumination distributions to be directed to a target region for performing intensity modulated radiation therapy is presented, wherein the computer program comprises program code means for causing a device as defined in claim 1 to carry out the steps of the method as defined in claim 12, when the computer program is run on a computer controlling the device.

It shall be understood that the device of claim 1, the apparatus of claim 11, the method of claim 12, and the computer program of claim 13 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
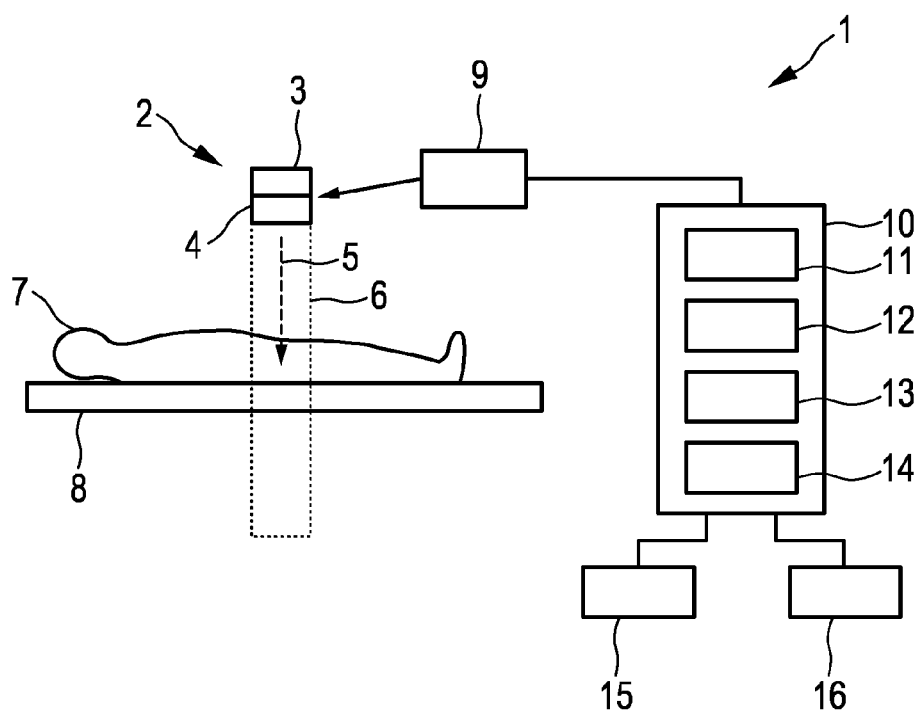
FIG. 1 shows schematically and exemplarily an embodiment of an apparatus for performing IMRT.

FIG. 1 shows schematically and exemplarily an embodiment of an apparatus 1 for performing IMRT. The apparatus 1 comprises a radiation device 2 for providing illumination distributions to be directed to a target region within a person 7 lying on a support means like a table 8. The radiation device 2 emits radiation 5 forming the illumination distributions and is mounted on a rotatable gantry 6, in order to rotate the radiation device 2 around the person 7.

The apparatus 1 comprises a device 10 for determining illumination distributions to be directed to the target region within the person 7 for performing the IMRT. The device 10 comprises a fluence map providing unit 11 for providing several fluence maps for several rotational positions of the radiation device 2 around the person 7. Thus, the fluence map providing unit 11 provides for each IMRT beam angle a two-dimensional fluence map. In particular, the fluence map providing unit 11 is adapted to perform a fluence map optimization (FMO) algorithm, which calculates for each treatment beam angle, i.e. for each rotational position of the radiation device 2, a two-dimensional ideal fluence map by solving a positivity-constraint optimization problem. For determining the two-dimensional fluence maps the target region is preferentially delineated and segmented in a three-dimensional image of the person including the target region, wherein the fluence map optimization algorithm optimizes an objective being a function of the radiation dose distribution within the person 7. Preferentially, the fluence map optimization algorithm determines the two-dimensional fluence maps such that the delineated and segmented target region receives a predefined radiation dose, whereas surrounding parts of the person 7, which should not be treated, receive a radiation dose, which is as small as possible. The fluence map providing unit 11 can be adapted to use a known FMO algorithm like the algorithm disclosed in the article "Optimization of stationary and moving beam radiation therapy techniques" by A. Brahme, Radiotherapy and Oncology, 12: pages 129 to 140 (1988), which is herewith incorporated by reference. However, also other known FMO algorithms may be used like the algorithms disclosed in the articles "Iterative Approaches to Dose Optimization" by D. M. Shepard et al., Physics in Medicine and Biology, 45:(1): pages 69 to 90 (1999) and "Optimizing the planning of intensity-modulated radiotherapy" by S. Webb, Physics in Medicine and Biology, 39: (12): pages 2,229 to 2,246 (1994), which are herewith incorporated by reference.

The target region can be automatically delineated and segmented, or it can be semi-automatically or completely manually delineated and segmented by using an input unit 15 like a keyboard, a mouse, a touch screen, et cetera and a display 16. The fluence map providing unit 11 can also be a storing unit, in which the two-dimensional fluence maps for the different rotational positions of the radiation device 2 are stored already or it can be a receiving unit for receiving the two-dimensional fluence maps from another device, which has calculated the two-dimensional fluence maps, by a wired or wireless data connection, wherein the receiving unit can provide the received two-dimensional fluence maps.

Figure 2:
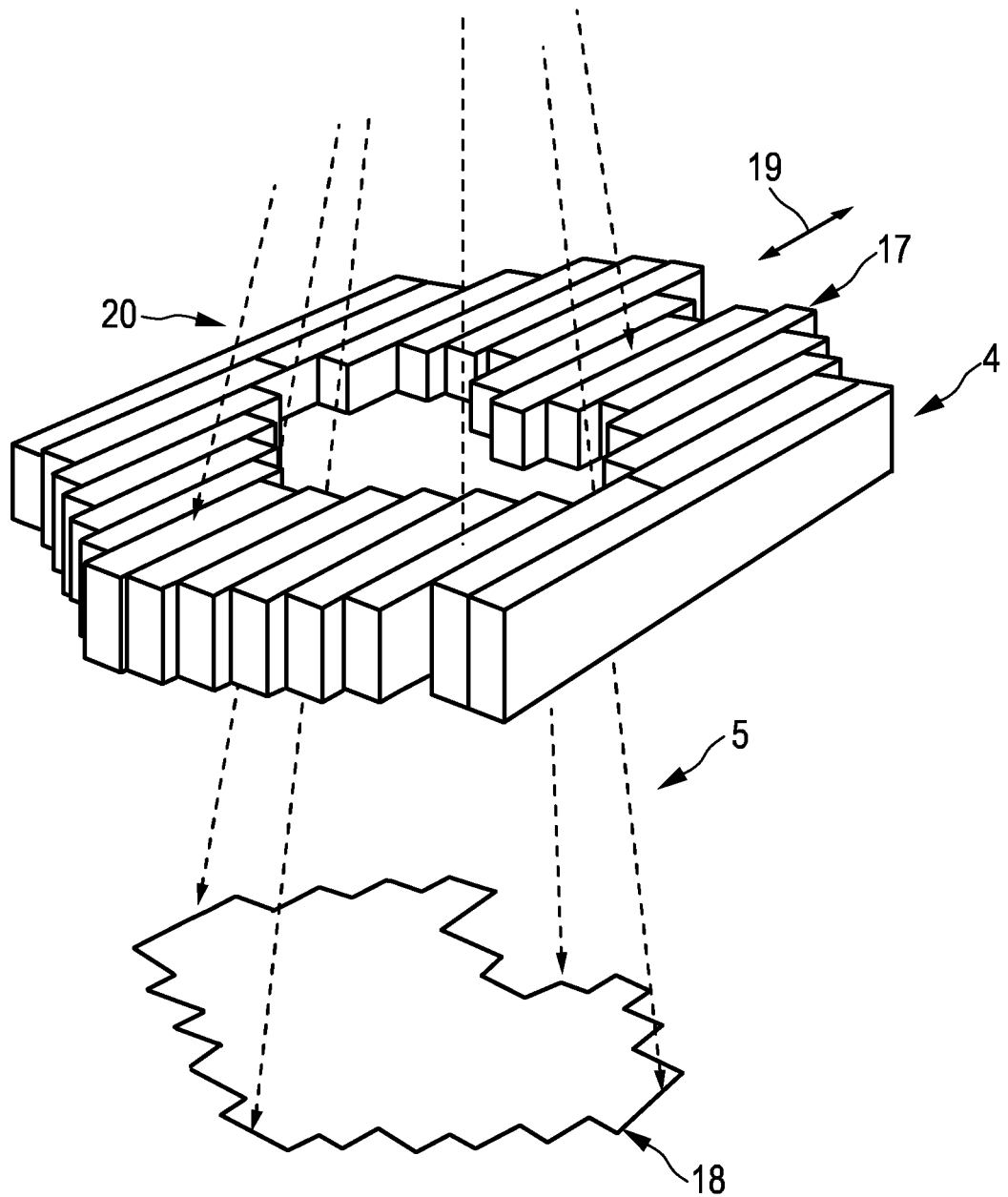
FIG. 2 shows schematically and exemplarily a multileaf collimator of the apparatus shown in FIG. 1.

The device 10 further comprises a layered graph structure providing unit 12 for providing a layered graph structure. The layered graph structure comprises layers with nodes, wherein the nodes of a layer represent extensions $b_r$ of an illumination distribution, which are realizable by the radiation device 2, along a line, wherein different layers correspond to different parallel lines and wherein nodes of adjacent layers are connected by graph edges, to which first weights $e_r$ are assigned. In this embodiment, the radiation device 2 comprises a combination of a radiation source 3 and a multileaf collimator 4, wherein the lines, along which the extensions $b_r$ of the illumination distributions are defined, are aligned along the leafs of the multileaf collimator 4 and wherein realizable positions of the leafs of the multileaf collimator 4 define realizable extensions $b_r$ of the illumination distribution along the respective line. The leafs 17 of the multileaf collimator 4, which are schematically and exemplarily illustrated in FIG. 2, are movable along the directions indicated by the double arrow 19, such that a realizable extension $b_r$ of an illumination pattern 18 along a line being parallel to the directions 19 is defined by the possible positions of the leafs 17. The positions of the leafs 17 define therefore the opening or shape of the illumination distribution 18.

The multileaf collimator 4 is a flexible blocking device for selecting only a part of an incident broad photon beam 20 emitted by the radiation source 3. The selected part forms the radiation 5 and the respective illumination distribution 18. The resulting beam 5 has a constant intensity level in the selected part, i.e. the respective illumination distribution 18 substantially only has two fluence values, i.e. zero and a fluence value being larger than zero. By subsequently superposing multiple openings of the multileaf collimator 4, i.e. by superposing multiple resulting illumination distributions 18, which may also be regarded as being segments, an arbitrary fluence map can be generated for the respective illumination direction, in order to approximate arbitrary profiles in the person 7. The positions of the leafs 17 are restricted due to physical limitations and constraints like the minimum interleaf gap, the leaf interdigitation, the leaf maximum center over-travel, et cetera. In order to generate deliverable apertures, i.e. realizable illumination distributions 18, the physical limitations and constraints are taken into account by using the layered graph structure during the process of determining the illumination distributions, which may also be regarded as being a leaf-sequencing process.

The device 10 further comprises an extensions determination unit 13 for determining extensions $b_r$ of an illumination distribution along the parallel lines for several illumination distributions, wherein the extensions determination unit 13 is adapted to determine the extensions $b_r$ for an illumination distribution by determining a sequence of nodes connected by the graph edges through the layered graph structure, which optimizes a cost function that depends on the first weights $e_r$ assigned to the graph edges connecting the nodes of the sequence. Moreover, the device 10 comprises a second weights determination unit 14 for determining second weights w defining the fluences of the illumination distributions, which are to be determined for the respective rotational position of the radiation device 2 and for which the extensions $b_r$ have been determined, such that a deviation between the provided respective fluence map and a combination m of the illumination distributions having the determined extensions $b_r$ and the fluences defined by the second weights w is minimized.

The layered graph structure providing unit 12, the extensions determination unit 13 and the second weights determination unit 14 are adapted such that the provision of the layered graph structure, the determination of the extensions $b_r$ and the determination of the second weights w are repeatedly performed, wherein the layered graph structure is repeatedly provided, i.e. repeatedly determined, by repeatedly determining the first weights. Thus, the provision of the layered graph structure, the determination of the extensions and the determination of the second weights can be iteratively performed, until an abort criterion is fulfilled. The abort criterion may be that a predefined number of iteration steps has been reached and/or that the deviation between the provided fluence map and the combination m of the illumination distributions having the determined extensions $b_r$ and the fluences defined by the second weights w is smaller than a predefined threshold.

The layered graph structure providing unit 12 is adapted to determine a deviation function $f$ being indicative of a deviation between the respective provided fluence map and the combination m of illumination distributions having the determined extensions $b_r$ and the fluences defined by the second weights w and to determine the first weights $e_r$ depending on the deviation function $f$. In this embodiment, the layered graph structure providing unit 12 is adapted to determine the first weights $e_r$ depending on gradients, i.e. local gradients, of the deviation function $f$ with respect to pixels of the illumination distributions. The gradients information of the deviation function $f$ is used to minimize the difference between the respective provided fluence map and the combination m of illumination distributions. In particular, the layered graph structure providing unit 12 is adapted to determine a first weight $e_r(b_r, b_{r-1})$ for a graph edge depending on the gradients of the deviation function $f$ for pairs of adjacent extensions $b_r$, $b_{r-1}$ represented by the nodes connected by the respective graph edge at all pixel locations. The deviation function is preferentially a function being indicative of the sum of squared differences between the respective provided fluence map and the combination m of illumination distributions having the determined extensions $b_r$ and the fluences defined by the second weights w.

The device 10 is adapted to find a deliverable fluence map model, i.e. a deliverable combination m of the illumination distributions having the determined extensions $b_r$ and the fluences defined by the second weights w, which approximates the provided fluence map, i.e. the given target fluence map provided by the fluence map providing unit 11 for the respective rotational position of the radiation device 2. In this embodiment, the model for the fluence map is represented by a column vector m. The column vector m represents several rows or columns of the fluence map model, which are stacked on each other. The fluence map model is formed by a set of N multileaf collimator openings, i.e. N illumination distributions or segments, wherein each one is associated with a second weight $w_i$, which may also be regarded as being a segment weight. The leaf collimator openings and the second weights, which define the fluences, are adjustable machine parameters. As the multileaf collimator is assumed to either block the fluence or to be fully open for a pixel position in m, the elements of the respective segment are considered binary. The n-th segment opening can be denoted by $s_n$, wherein a vector element of this vector $s_n$ is zero or one depending on whether the respective pixel is blocked or not by the multileaf collimator. A binary matrix S can be defined, wherein the columns of this binary matrix are formed by the vectors $s_n$. The second weight for the n-th segment or illumination distribution can be denoted by $w_n$, wherein all second weights can be collected in the vector w. The fluence map model can then be defined as a linear combination of the binary matrix S with the corresponding second weights in accordance with following equation:

$$m = S \cdot w. \tag{1}$$

If it is assumed that the movement directions 19 of a collimator leaf pair are within a row of the fluence map image, a binary segment opening $s_n$ can be deposed into R smaller binary sub-vectors $b_r$, one for each row, wherein each binary sub-vector $b_r$ represents an extension along the respective row, i.e. in this embodiment along the respective row, and wherein R indicates the total number of pairs of leafs 17 or rows provided by the multileaf collimator 4.

The layered graph structure is preferentially used to determine segment openings $s_n$, which satisfy all physical constraints and optionally also further user-defined constraints. In this embodiment each layer of the graph represents one row, i.e. one pair of leafs, of the multileaf collimator grid. For each layer a certain number of nodes is used to represent all realizable leaf pair positions in multileaf collimator coordinates. In particular, the opening between the left leaf position and the right leaf position in the r-th collimator row determines the binary pattern of the respective sub-vector $b_r$, i.e. the respective extension of the illumination distribution along the respective row, wherein all opened pixels are identified by 1's and pixels shielded by leafs 17 of the multileaf collimator 4 are identified by 0's. Those constraints that effect the positions of opposing leafs 17 in a single row like single opening, minimum gap, maximum over-travel et cetera reduce the number of potential opening combinations in $b_r$. The graph edges connect nodes of adjacent layers, wherein a corresponding first weight, which can also be regarded as being a cost, is assigned to each graph edge.

For determining the first weights the layered graph structure providing unit 12 can use a fluence map gradient-based objective, i.e., for instance, the deviation function $f$ can be the sum of squared differences between the provided ideal target fluence map and the actual modeled fluence map m, wherein this deviation function $f$, which can also be regarded as being an objective function, can be used for leaf-sequencing by determining the gradient of this function with respect to the fluence map pixels. The gradient information of the deviation function $f$ is used to minimize the difference between the ideal target fluence map and the fluence model m. The first weights $e_r(b_r, b_{r-1})$ are preferentially determined for and assigned to the graph edges of adjacent nodes $b_r$ and $b_{r-1}$ by providing local gradient values of the deviation function $f$ for valid openings $b_r$ and $b_{r-1}$. Here, a decomposition of the gradient of the deviation function $f$ into a sum of local, i.e. pairs of adjacent $b_r$ contributions is assumed. Thus, the objective function, i.e. the deviation function, with respect to the fluence map pixels can be used to determine the best search direction.

The layered graph structure providing unit 12 is adapted to assign an infinite, i.e. invalid, first weight $e_r(b_r, b_{r-1})$ to a graph edge indicating an impossible transfer from one of the nodes connected by the graph edge to another of the nodes connected by the graph edge, if the combination of extensions $b_r, b_{r-1}$ of the illumination distribution represented by these nodes is not realizable by the radiation device 2, for instance, by interdigitation violation. For instance, if machine constraints forbid a combination of openings, i.e. of extensions $b_r$ and $b_{r-1}$ between the r-th row and its predecessor row, an infinite, i.e. invalid, value can be assigned to the corresponding graph edge as the first weight.

Figure 3:
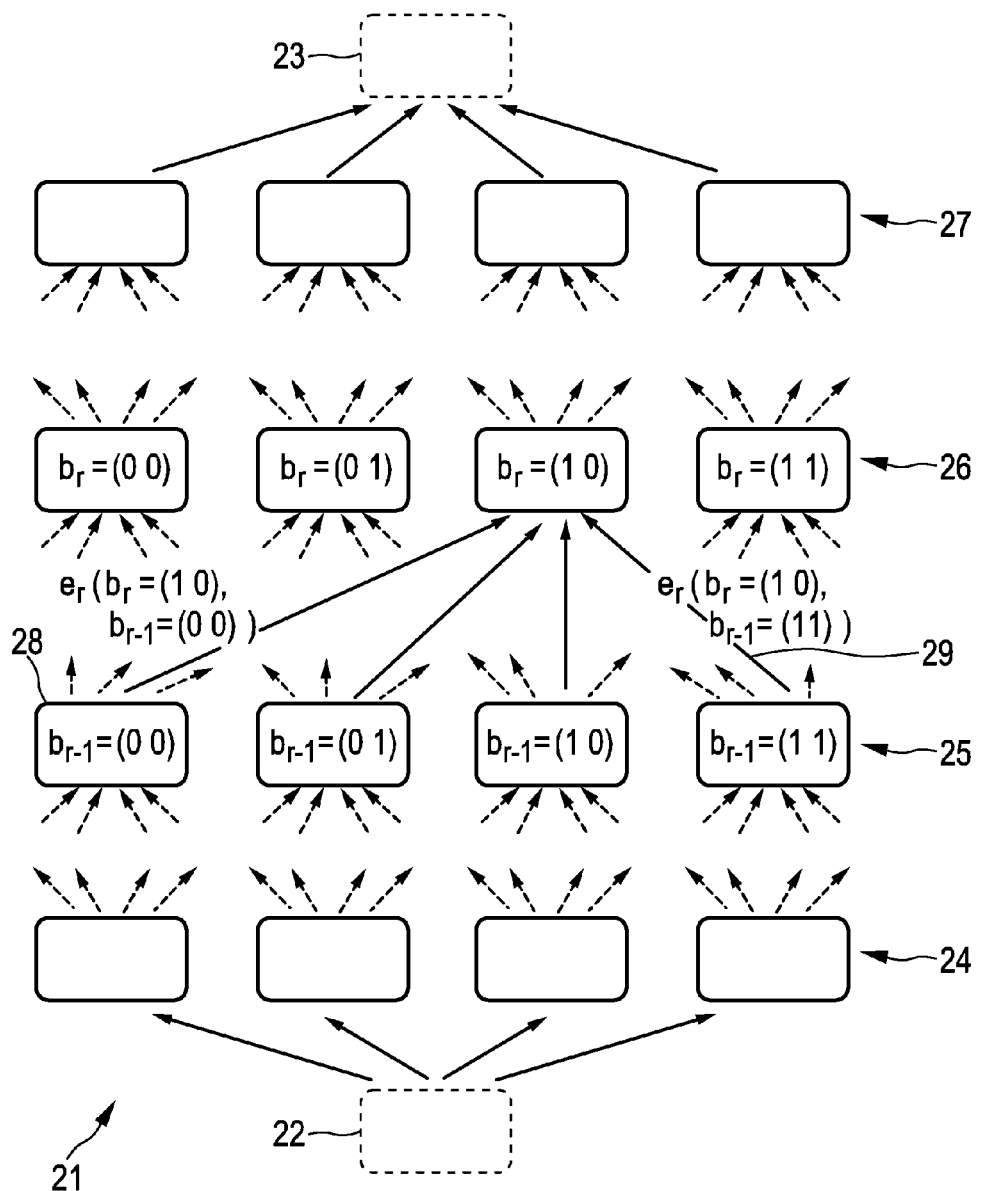
FIG. 3 illustrates exemplarily an embodiment of a layered graph structure.

FIG. 3 illustrates a possible layered graph structure 21, which may be provided by the layered graph structure providing unit 12. In FIG. 3 the layered graph structure 21 comprises several layers 24 . . . 27 with different nodes 28 and graph edges 29. For the r-th layer 26 and for the (r−1)-th layer 25 extensions, i.e. corresponding binary vectors, $b_r$, $b_{r-1}$ are exemplarily indicated. Moreover, for some graph edges 29 first weights $e_r$ are exemplarily indicated.

Moreover, in FIG. 3 the boxes 22, 23 denote a start and an end, respectively, of a sequence of nodes connected by the graph edges through the layer structure 21, which optimizes a cost function that depends on the first weights assigned to the graph edges connecting the nodes of the sequence. Thus, the boxes 22, 23 denote a virtual start node and a virtual end node, respectively, wherein a shortest path search in the layered graph structure 21 starts at the virtual start mode 22 and terminates at the virtual end node 23.

In FIG. 3 the layered graph structure 21 represents a set of illumination distributions having maximally R rows and C columns, wherein in this simple example R=4 and C=2. The number of nodes per layer is defined by the number of valid leaf pair opening combinations for C pixels in an image row being, in this example, (0 0), (0 1), (1 0) and (1 1). Each node 28 is characterized by the binary row opening pattern, i.e. the respective extension $b_r$. The node with $b_{r-1}$ in the (r−1)-th layer is connected with a node with $b_r$ in the r-th layer with a directed graph edge 29, if $b_r$ and $b_r$ represent a valid configuration for adjacent leaf pairs, for instance, a configuration without interdigitation. The corresponding edge weight, i.e. the corresponding first weight, is $e_r(b_r, b_{r-1})$.

The layered graph structure providing unit 12 is preferentially further adapted to assign regularization values $P_r$ to the graph edges. The regularization values may depend on deviations between the extensions $b_r, b_{r-1}$ of the illumination distributions represented by the nodes connected by the respective graph edges. The regularization values, which can also be regarded as being regularization weights, can be added to the first weights, which are preferentially local gradient-based weights. The regularization values can be used to enforce smooth opening contours and/or larger opening areas. For instance, following regularization term may be added to the first weights $e_r$ to enforce smoother segment opening contours:

$$P_r = \frac{\|b_r - b_{r+1}\|_1}{\frac{1}{2} \cdot (\|b_r\|_1 + \|b_{r+1}\|_1)}. \tag{2}$$

A weighting parameter α can be used to tune for a best tradeoff between the first weight $e_r$ and the smoothing penalization $P_r$. The weighting parameter α may be determined by trying different weighting parameters α and selecting the weighting parameter α, which leads to the best approximation of the ideal fluence map provided by the fluence map providing unit 11.

Figure 4:
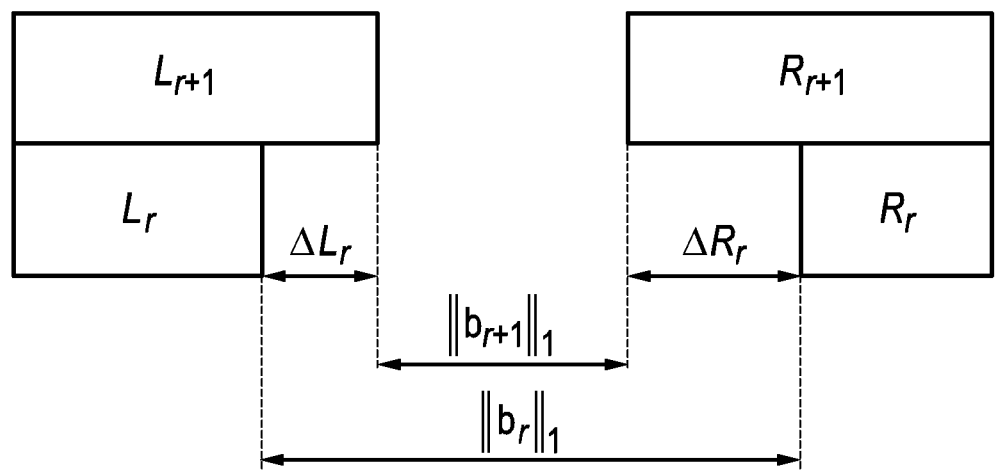
FIG. 4 illustrates different parameters used for regularization.

FIG. 4 schematically and exemplarily illustrates the regularization for smoother segment opening contours. In FIG. 4 $L_r$ and $R_r$ represent left and right leafs of the r-th pair, while $b_r$ indicates the corresponding leaf pair opening, i.e. the corresponding extension of an illumination distribution along a line defined by the two leafs $L_r$ and $R_r$. $L_{r+1}$ and $R_{r+1}$ represent left and right leafs of the adjacent (r+1)-th pair, while $b_{r+1}$ indicates the corresponding leaf pair opening. The proposed penalization weight $P_r$ enforces smoother segment opening contours by minimizing left and right adjacent leaf tips distances $\Delta L_r$ and $\Delta R_r$. The final combined edge weights, i.e. the combination of the respective first weight and the regularization value by using the weighting parameter α, are used to find the "less costly" path through the layered graph structure 21, i.e. in terms of network theory the "shortest path", and thus the best segment opening as will be described in the following.

In order to generate an optimal set of deliverable openings $s_n$, wherein each opening $s_n$ is defined by a sequence of extensions $b_r$, the extensions determination unit 13 preferentially applies a shortest-path search, in order to find the best path through the layered graph structure 21. Those paths containing graph edges associated with an infinite weight are not considered. Moreover, a node without incoming or outcoming graph edges is also not considered. The sequence of nodes along the shortest path, i.e., in this embodiment, corresponding to the smallest sum of traversed weights assigned to the graph edges, correspond to a solution of the segment optimization problem, wherein each node of the sequence of nodes is associated with a binary image row opening. During graph traversal the dynamic programming procedure determines for each visited node the shortest partial path. This principle keeps the search complexity linear in the number of image rows instead of, for instance, an exponential growth. For performing the graph search search algorithms like a breadth-first, depth-first style algorithm can be used. Additional heuristics like A*-search or beam-search pruning may be used to further speed-up the search.

The constrained optimization of segment openings is preferentially performed segment-wise. In particular, in a segment-by-segment strategy one set of segment openings is optimized while keeping the remaining segment openings of the segment binary matrix S fixed. For example, let the n-th segment opening $s_n$ be the subject of the constrained optimization procedure. In this case an intermediate fluence map $\hat{m}_n^-$ may be defined by excluding the segment opening $s_n$ and the second weight $w_n$ from the determination of the fluence map model (cf. equation (1)). In general, the goal with optimizing $s_n$ is equal to finding a feasible direction vector s such that a decrease in the deviation function $f$ is achieved, i.e. $f(\hat{m}_n^-) > f(\hat{m}_n^- + ws)$, with a segment weight parameter w. This approach is similar to the determination of the search direction in line search based iterative optimization, where the segment weight parameter w is proportional to the step width and the search direction vector s is constrained by the machine properties. However, the approach differs from classical line search methods by allowing the second weights determination unit 14 to optimize all second weights w after optimization of an individual segment opening $s_n$.

The change of the deviation function $f$ when moving from the intermediate fluence map $\hat{m}_n^-$ along the direction s with a weight w is given by:

$$\delta f(ws)|_{\hat{m}_n^-} = f(\hat{m}_n^- + ws) - f(\hat{m}_n^-). \quad (3)$$

A decomposition of the change of the deviation function $f$ into a sum of local, i.e. pairs of adjacent $b_r$, contributions is preferentially considered for all segment rows R in accordance with following equation:

$$\delta f(ws)|_{\hat{m}_n^-} = \sum_{r=1}^{R} \delta f_r(b_r, b_{r-1})|_{\hat{m}_n^-}. \quad (4)$$

The change of the deviation function $f$ is therefore preferentially determined for pairs of adjacent extensions $b_r$, $b_{r-1}$. Such decomposition into a sum of local contributions allows employing the dynamic programming procedure within the layered graph structure, which keeps the search complexity linear.

The determination of the layered graph structure by the layered graph structure providing unit 12 uses preferentially local first weights $e_r(b_r, b_{r-1})$ for graph edges depending on the expression $\delta f_r$ (cf. equation (4)) of the deviation function $f$ for valid pairs of adjacent extensions $b_r$, $b_{r-1}$ and an infinite, i.e. invalid, value for combinations of adjacent extensions $b_r, b_{r-1}$ representing configurations forbidden by the radiation device 2 in accordance with following equation:

$$e_r(b_r, b_{r-1}) = \begin{cases} \delta f_r(b_r, b_{r-1})|_{\hat{m}_n^-} & \text{valid} \\ \infty & \text{forbidden} \end{cases}. \quad (5)$$

Using such function $e_r(b_r, b_{r-1})$ a constrained optimization problem can be reformulated as an unconstrained segment optimization problem to find the optimal n-th segment opening $\hat{s}_n$ for feasible extensions $(b_1 \ldots b_R)^T$:

$$\hat{s}_n = \begin{pmatrix} \hat{b}_1 \\ \vdots \\ \hat{b}_R \end{pmatrix} = \text{argmin}_{(b_1 \ldots b_R)^T} \left\{ \sum_{r=1}^{R} e_r(b_r, b_{r-1}) \right\}. \quad (6)$$

In particular, the regular and local image-row-by-row structure of equation (6) allows for an equivalent formulation as a shortest-path-search in a directed, non-cyclic graph of R node layers. For example, in the r-th layer, each node is associated with a feasible opening $b_r$ of a leaf pair in the r-th collimator row. Each node in the r-th layer is connected to nodes in the previous layer via edges. Each edge is related to a weight; the weight of an edge that connects two nodes associated with leaf pair openings $b_r$ and $b_{r-1}$ is given by the function $e_r(b_r, b_{r-1})$ in equation (5). For a shortest-path-search in the graph, all edges associated with an infinite weight are not considered; a node without incoming or outgoing edges is not considered. The set of nodes associated with the image row openings $(b_1 \ldots b_R)^T$ on the shortest path, i.e. smallest sum of traversed edge weights, corresponds to an optimal solution $\hat{s}_n$ of the problem in equation (6).

In this embodiment the expression $\delta f$ (equation (3)) is preferentially approximated by a first order Taylor series in accordance with following equation:

$$\delta f(ws)|_{\hat{m}_n^-} \approx w \cdot (s^T \cdot \nabla_m f|_{\hat{m}_n^-}). \quad (7)$$

In another embodiment also higher orders of the Taylor series may be applied, in particular, the second order. The gradient information $\nabla_m f|_{\hat{m}_n^-}$ is exploited to determine the local gradients for valid pairs of adjacent extensions $b_r$, $b_{r-1}$ and the optimal descent of the deviation function from the first weights $e_r(b_r, b_{r-1})$. Preferentially, a spherical treatment, i.e. using only one gradient to determine the first weights, is performed for the first row r=1.

An optional regularizer may be added to the deviation function $f$ to give preference to, for instance, large openings or smooth opening contours. Any regularization term, such as the regularization term $P_r$ (cf. equation (2)) preferentially follows an expression of the same locality as the first weights $e_r(b_r, b_{r-1})$.

The second weights determination unit 14 is preferentially adapted to assume a fixed set of segment openings $s_n$ forming the segment binary matrix S, when determining and optimizing the second weights w, which can also be regarded as being segment weights. The second weights are non-negative values such that a lower bound constraint optimization problem is preferentially solved. However, the constraint optimization problem can be converted into an unconstrained problem by variable substitution. For example, the constrained optimization problem, i.e. to determine optimized second weights w from the deviation function $f$ with respect to initial second weights $w_0$ with $w \geq w_0$, can be transformed into an unconstrained optimization problem by the variable substitution $w \rightarrow w_0 + (\tilde{w})^2$ for feasible segment matrices S:

$$w = w_0 + \lfloor \text{argmin}_{\tilde{w} \in R^N} \{ f(S \cdot (w_0 + (\tilde{w})^2)) \} \rfloor. \quad (8)$$

The expression $(\tilde{w})^2$ denotes taking the square of the new parameter vector $\tilde{w}$ element-wise, thus $(\tilde{w})^2$ has only positive values. An optional regularizer may be added to the determination routine of $\tilde{w}$ to penalize unwanted solutions for $\tilde{w}$, for instance, large values in w that would correspond to very long beam-on times. Quadratic convergent non-linear unconstrained optimizers like a conjugated gradient optimizer or a L-BFGS optimizer can be applied to the inner optimization problem of equation (8) by the second weights determination unit 14. Preferentially the computation involves the first order derivatives $\nabla_w f$ of the deviation function $f$ with respect to the transformed segment weights $\tilde{w}$, and in some cases the second order information. The gradient of the fluence map based deviation function $f$ with respect to the transformed segment weights $\tilde{w}$ can be easily obtained from the gradient with respect to the original second weights w from the gradient chain rule:

$$\nabla_{\tilde{w}} f = 2 \text{Diag}(\tilde{w}) \cdot \nabla_w f. \quad (9)$$

In this expression $\text{Diag}(\tilde{w})$ denotes a diagonal matrix that is constructed from the elements of the transformed segment weights vector $\tilde{w}$.

In particular, the algorithms disclosed in the article "A comparison of three optimization algorithms for intensity modulated radiation therapy" by D. Pflugfelder et al., Zeitschrift für medizinische Physik, volume 18, number 2, pages 111 to 119 (2008) can be used by the second weights determination unit 14, which is herewith incorporated by reference.

The layered graph structure providing unit 12, the extensions determination unit 13 and the second weights determination unit 14 are preferentially adapted to be operated in an iterative procedure, in which the machine parameters, i.e. S and w, are optimized in an iterative technique that toggles between the optimization of segment openings $s_n$ performed by the extensions determination unit 13 and the optimization of the second weights performed by the second weights determination unit 14. For instance, firstly second weights are kept fixed and segment openings are optimized, wherein then segment openings are kept fixed and second weights are optimized, and so on. In particular, the matrix S that contains the leaf openings of all segments, i.e. of all illumination distributions to be determined, is optimized in a column-by-column, i.e. segment opening-by-segment opening, strategy, while keeping the remaining elements of the matrix S fixed. After optimization of each individual column $s_n$ of the matrix S all second weights w may be re-optimized by the second weights determination unit 14 as described above. After all N columns in the matrix S have been optimized by this strategy, the entire procedure might be re-iterated, e.g. by re-starting with the first column of matrix S. The iterative procedure is preferentially performed until an abort criterion is fulfilled like that a desired threshold of the deviation function, i.e. the ideal target fluence map is sufficiently approximated by the fluence model m, is reached. The segment openings $s_n$ and the second weights w initially have initial values, which may be based on a priori knowledge, which may be provided by a user. However, initial values can also be provided in another way. For instance, arbitrary initial values may be used, or initially it may be assumed that the leaf pairs are completely closed such that, for instance, S=0. In this case the iterative strategy corresponds to a column generation, wherein with each generation of a new segment opening $s_n$ a further column vector of the matrix S is generated. The column generation procedure is preferentially performed until an abort criterion is fulfilled like that a desired maximum number of segments $s_n$ has been reached. The IMRT apparatus 1 further comprises a control unit 9 for controlling the radiation source device 2 in accordance with the determined illumination distributions. In particular, after the device 10 has determined the segment openings $s_n$ and the corresponding second weights w, which define the illumination distributions approximating the ideal provided fluence map, the control unit 9 controls the radiation device 2 such that at the respective rotational position of the radiation device 2, the illumination distributions, which have been determined for this rotational position of the radiation device 2, are directed to the target region for performing the IMRT.

Figure 5:
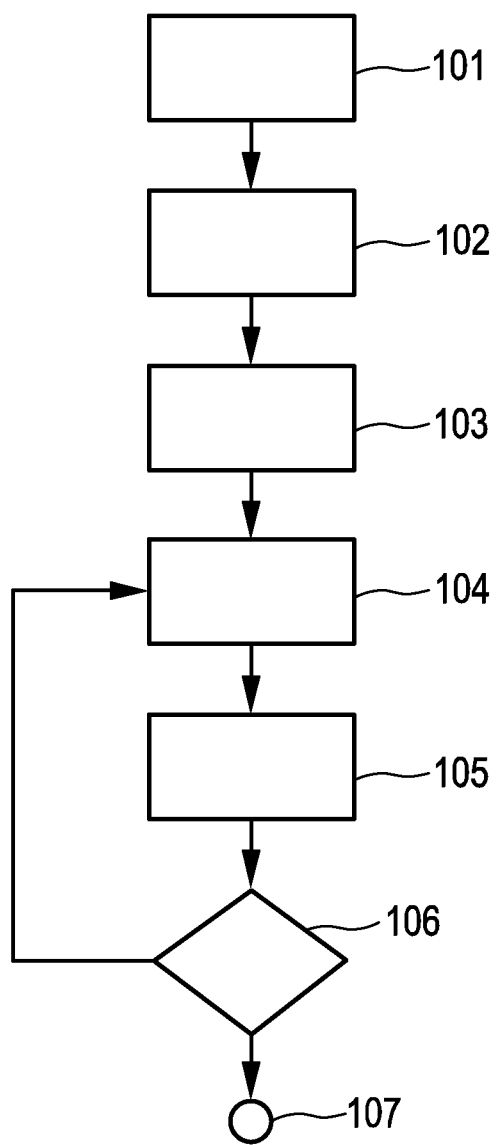
FIG. 5 shows a flowchart exemplarily illustrating an embodiment of a method for determining illumination distributions to be directed to a target region for performing IMRT, FIG. 6 schematically and exemplarily shows a provided ideal fluence map.

In the following an embodiment of a method for determining illumination distributions to be directed to a target region for performing IMRT will exemplarily be described with reference to a flow chart shown in FIG. 5.

In step 101 several ideal fluence maps are provided for different rotational positions of the radiation device, wherein each fluence map should be approximated by a combination of illumination distributions to be determined. In step 102 the method is initialized, in particular, initial illumination distributions defined by segment openings $s_n$ and second weights w are provided for each rotational position of the radiation device. In step 103 a layered graph structure is provided, wherein the layered graph structure comprises layers with nodes, wherein the nodes of a layer represent extensions $b_r$ of an illumination distribution along a line, which are realizable by the radiation device, wherein different layers correspond to different parallel lines and wherein nodes of adjacent layers are connected by graph edges, to which at least first weights $e_r$ are assigned. Preferentially, also regularization values are assigned to the graph edges. The lines preferentially correspond to rows of the illumination distributions defined by pairs of leafs of the multileaf collimator.

In step 104 extensions $b_r$ of the illumination distributions $s_n$ along the parallel lines are determined for several illumination distributions and for the several rotational positions. In step 105 second weights defining the fluences of the illumination distributions, for which the extensions $b_r$ have been determined, are determined for the rotational positions by the second weights determination unit such that a deviation between the fluence map provided for the respective rotational position and a combination m of the corresponding illumination distributions having the determined extensions $b_r$ and the fluences defined by the second weights w is minimized. In step 106, it is determined whether an abort criterion has been fulfilled, wherein, if this is the case, the method for determining the illumination distribution ends in step 107. Otherwise, the method iteratively continues with step 104. The steps are performed for each rotational position of the radiation device such that for each rotational position a set of illumination distributions defined by the segment openings $s_n$ and the second weights w is determined, which approximates the ideal provided fluence map provided for the respective rotational position of the radiation device.

To implement IMRT safely and efficiently, the characteristics of the multileaf collimator, the associated delivery systems and the limitations of each system when applied to IMRT have to be understood. It is known to implement a two-dimensional intensity-modulated beam delivery method using multiple static segmented fields, i.e. using the "step-and-shoot-approach". Starting with a desired "ideal" fluence distribution, i.e. the ideal fluence map, the known method generates a sequence of segmented fields to deliver a multiple-level intensity using a multileaf collimator. An essential component of this radiation treatment planning algorithm is a means for determining the leaf positioning sequence that will produce the desired beam fluence pattern. However, by this known method the multileaf collimator's physical constraints and limitations like the interleaf minimum gap, the leaf interdigitation, the maximum leaf over-travel, et cetera and additional user-defined soft constraints are not taken into account during the leaf sequencing process, which can also be regarded as being a conversion process or a segmentation process. In particular, the known leaf sequencing process creates a discretized multiple-level fluence approximation of the ideal fluence map, whereupon a set of segmented fields is created, and only at the end of the process the segments are checked and post-processed to ensure that all multileaf collimator constraints are satisfied. With such a strategy many non-deliverable segments are disregarded, which subsequently leads to radiotherapy plan degradation. The device and method for determining illumination distributions to be directed to a target region for performing IMRT described above with reference to FIGS. 1 to 5 overcome this problem.

The device and the method are preferentially adapted to apply a column generation approach to radiation therapy treatment planning proposed in the article "A column generation approach to radiation therapy treatment planning using aperture modulation" by H. Edwin Romeijn et al., Journal on Optimization, Society of Industrial and Applied Mathematics SIAM J. OPTIM., volume 15, number 3, pages 838 to 862 (2005), directly for leaf-sequencing. This leads to a finally generated set of segments, i.e. together with the second weights a set of illumination distributions, which are surely deliverable. Moreover, the device and method described above with reference to FIGS. 1 to 5 provide an extension of the algorithm by allowing to include additional soft constraints, which may be user-defined, by using the regularization values added to the layered graph structure, in order to, for instance, enforce smooth opening contours or large openings. In particular, the device and method are preferentially adapted to solve a constraint combinatorial optimization problem to find the best deliverable segment openings, wherein fluence map-based functional gradient information is used by the device and method and an optional regularizer may be added to an objective function to give preference to, for instance, large openings or smooth opening contours in the final solution. Given a new segment generated by solving the constraint combinatorial optimization problem, the corresponding weight, i.e. the corresponding second weight, is calculated by solving a constraint optimization problem. Here, a fluence-based functional gradient with respect to the segment weights, i.e. with respect to the second weights, can be used to guide the optimizer towards the minimum. These steps, i.e. the finding of best deliverable segment openings and the calculation of the corresponding second weights, are iteratively executed, until a maximum number of segments, which may be user-defined, is reached.

Figure 6:
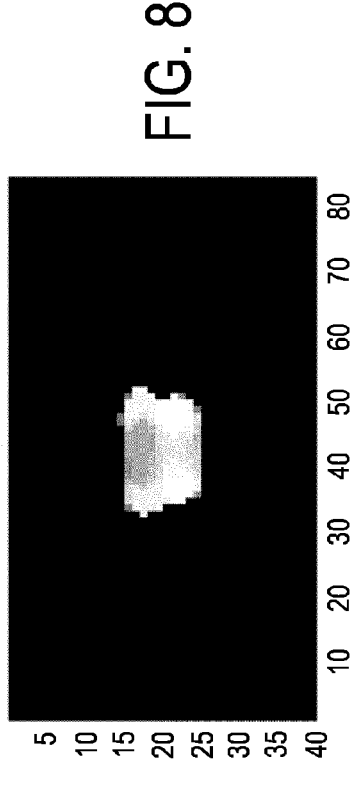
Figure 9:
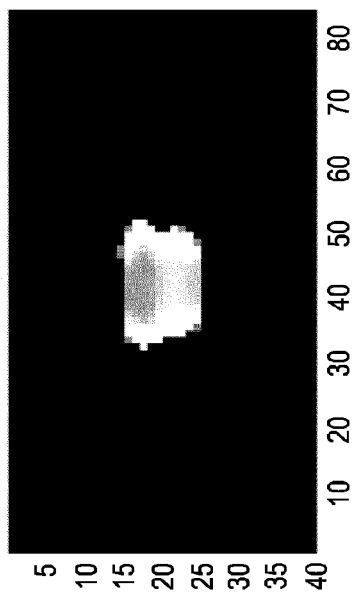
FIG. 9 shows a difference image calculated from the provided ideal fluence map shown in FIG. 6 and the model fluence map shown in FIG. 8.
Figure 7:
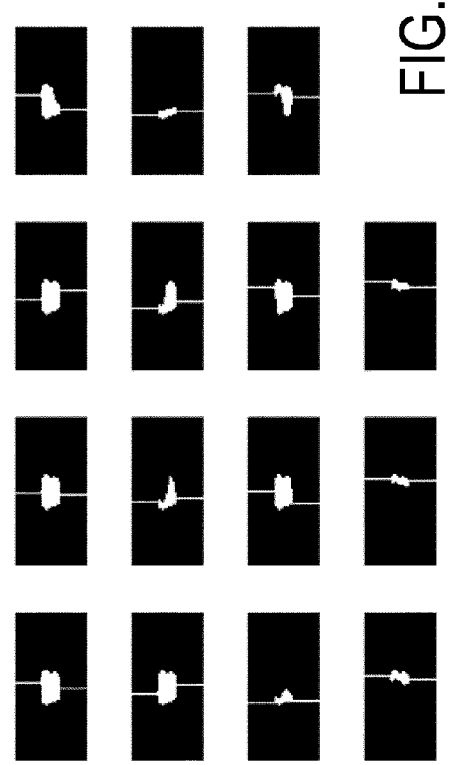
FIG. 7 shows schematically and exemplarily illumination distributions for approximating the provided ideal fluence map shown in FIG. 6.
Figure 8:
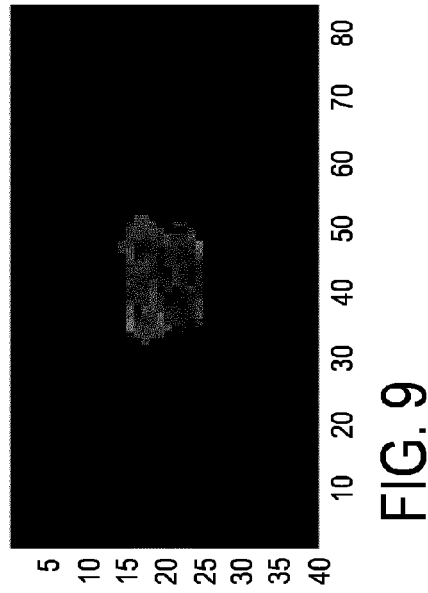
FIG. 8 shows schematically and exemplarily a model fluence map, which has been modeled by combing the illumination distributions shown in FIG. 7.

FIG. 6 shows schematically and exemplarily an ideal fluence map provided by the fluence map providing unit 11 for a certain rotational position of the radiation device 2. FIG. 7 shows schematically and exemplarily several illumination distributions determined for the rotational position of the radiation device 2 by the device 10, and FIG. 8 shows schematically and exemplarily a combination of the illumination distributions shown in FIG. 7 forming a modeled fluence map. FIG. 9 shows schematically and exemplarily a difference image calculated from the ideal provided fluence map shown in FIG. 6 and the modeled fluence map shown in FIG. 8. In this example the multileaf collimator has 40 leaf pairs, wherein each leaf has a width of 1 cm, the leafs minimum gap is 0.6 cm, the leaf interdigitation is 0.6 cm, the leaf maximum over travel is 12.5 cm and the maximum leaf movement resolution is 0.1 cm.

The provided two-dimensional fluence map, which can also be regarded as being a target fluence map, and the grid defined by the multileaf collimator are preferentially given in the same coordinate system and, if this is not the case, the ideal fluence map is preferentially transformed to match the geometry of the multileaf collimator. This geometrical transformation can be performed by using one of a multitude of possible resampling approaches. For instance, the pixel fluences of the provided ideal fluence map can be averaged along the leaf width, in order to define a new matrix that is consistent with the leaf width and, thus, in principle, deliverable. Moreover, the provided fluence map may be translated, rotated and/or distorted, in order to exactly match the grid of the multileaf collimator. Optionally, an additional low-pass filtering could be applied to the provided ideal fluence map, in order to reduce the noise, which may be present in the provided ideal fluence map.

Figure 10:
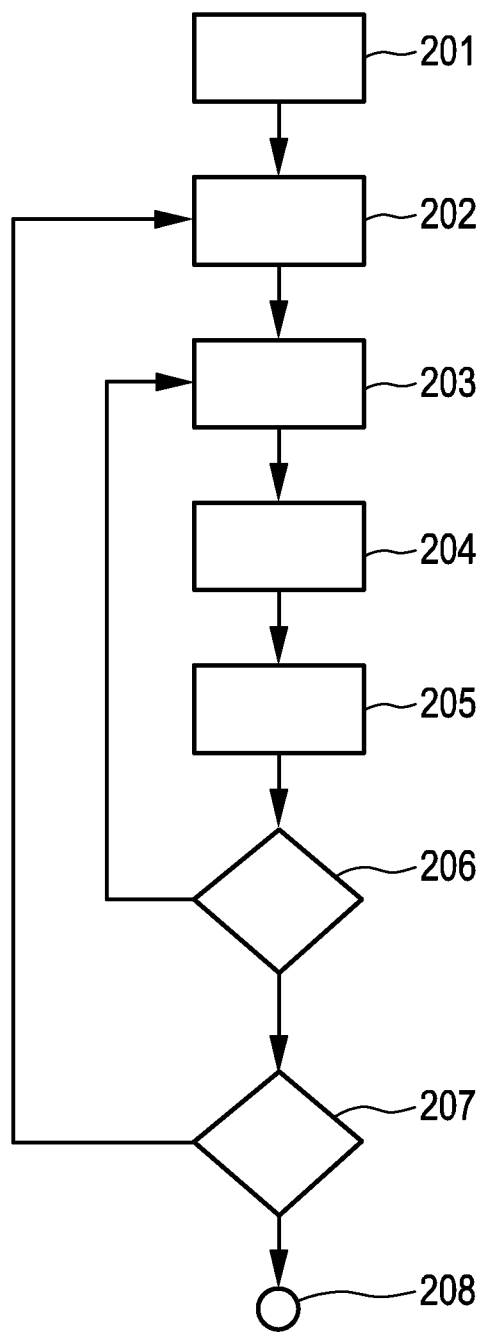
FIG. 10 shows a flowchart exemplarily illustrating a further embodiment of a method for determining illumination distributions to be directed to a target region for performing IMRT.

In an embodiment the layered graph structure providing unit 12 and the extensions determination unit 13 may be adapted such that, after the extensions determination unit 13 has determined extensions of an illumination distribution, a) nodes of the layered graph structure are selected based on a selection criterion which depends on the determined extensions, b) regularization values are assigned to the graph edges, and c) the extensions of the illumination distribution are determined again, wherein only the selected nodes are considered. This will in the following be explained with reference to a flowchart shown in FIG. 10.

In step 201, which corresponds to step 101, several ideal fluence maps are provided for different rotational positions of the radiation device, wherein each fluence map should be approximated by a combination of illumination distributions to be determined. In step 202 initial illumination distributions defined by the segment openings and the second weights are provided for a current rotational position of the radiation device. In step 203 a layered graph structure is provided for a current segment opening to be optimized, wherein the layered graph structure comprises layers with nodes, wherein the nodes of a layer represent realizable extensions of an illumination distribution along a line, which are realizable by the radiation device, wherein the different layers correspond to different parallel lines and wherein the nodes of adjacent layers are connected by graph edges, to which the first weights are assigned. The lines correspond to rows of the illumination distributions defined by pairs of leafs of the multileaf collimator. Moreover, in step 203 a segment opening, i.e. an illumination distribution, is determined by determining extensions of the illumination distribution along parallel lines, wherein these extensions are determined by determining a sequence of nodes connected by the graph edges through the layered graph structure, which optimizes a cost function that depends on the first weights assigned to the graph edges connecting the nodes of the sequence. In step 204 nodes of the layered graph structure are selected based on a selection criterion which depends on the determined extensions, regularization values like the regularization values defined in equation (2) are assigned to the graph edges, in particular, only to the graph edges that correspond to the selected nodes, and the extensions of the illumination distribution, i.e. of the current segment opening to be determined, are determined again, wherein only the selected nodes are considered, thereby generating an improved regularized illumination distribution, i.e. segment opening. In step 205 second weights defining the fluences of the illumination distributions, i.e. of the segment openings, are determined by the second weights determination unit such that a deviation between the fluence map corresponding to the current rotational position and a combination of the illumination distributions and the fluences defined by the second weights for the current rotational position is minimized. In step 206 it is determined whether for the current rotational position all segment openings have been optimized already. If this is not the case, the method continues with step 203. Otherwise, it is checked in step 207 whether the optimization procedure has been performed for all rotational positions. If this is not the case, the optimization procedure continues with step 202. Otherwise, the procedure ends in step 208. In step 206 it may also be checked whether a user-defined threshold of the deviation function has been reached, wherein, if this is not the case, the procedure may continue with step 203, even if the procedure has been performed for all segment openings, in order to further improve the segment openings.

From multi-criteria optimization theory it is well known that the minimization of a weighted linear sum of two or more conflicting objectives can lead to tedious weights tuning processes, in order to reach a Pareto solution which fits best the decision makers requirements. The optimization procedure described above with reference to FIG. 10 provides a multi-step approach that overcomes this problem. Steps 203 and 204 provide a two-steps lexicographic ordering scheme which first finds an optimal segment opening by minimizing a gradient-based functional only and which secondly refines its contours by optimizing a regularization-based functional. The selection criterion can be provided by using a user-defined maximum threshold for the gradient degradation, wherein by the selection process all possible nodes can be removed from the layered graph structure, which can lead to an unacceptable degradation of the previously determined gradient-based solution. The setting of such a threshold has a more intuitive meaning to the user than tuning weighting factors. Furthermore, by increasing the control of the planner over the regularization action, this lexicographic scheme can avoid tedious and cumbersome weights tuning processes and can lead to a better tradeoff between leaf sequencing accuracy and openings shape regularization. This concept of lexicographic ordering for segment generation could also be applied within a direct machine parameter optimization (DMPO) framework.

In particular, step 203 can be regarded as being a gradient-based segment opening optimization step. In order to generate an optimal deliverable opening, in this step a shortest-path search may be applied to find the best, i.e. less costly, path through the layered graph structure. Path containing edges associated with an infinite first weight are not considered; a node without incoming or outgoing edges is not considered. The set of nodes on the shortest path, i.e. having the smallest sum of traversed first edge weights, corresponds to the solution of the segment optimization problem in step 203, wherein the nodes are associated with the binary image row openings. During graph traversal the dynamic programming procedure determines for each visited node the shortest partial path. This principle keeps the search complexity linear in the number of image rows, instead of an exponential growth. Any appropriate search algorithm can be used for the graph search like a breath-first, depth-first style algorithm. Additional heuristics like A*-search or beam-search pruning may be used to further speed-up the search.

Step 204 may be regarded as being a segment opening smoothing regularization step. After an optimal segment opening $b_r^{old}$ is generated in step 203, regularization is applied to refine its shape, for instance, to smoother the opening contour, in step 204. The layered graph structure may be modified by removing all non-selected nodes $b_r^>$, which can produce a gradient degradation higher than a user prescribed maximum threshold. For example, a portion $p \in [0,1]$ of the local gradient of the previously determined optimal opening $b_r^{old}$ can be used as a threshold:

$$\delta f_r(b_r^>)|_{\hat{m}_n} > (\delta f(b_r^{old})|_{\hat{m}_n} + p \cdot |\delta f(b_r^{old})|_{\hat{m}_n}|). \tag{10}$$

A comparison of the gradient degradation with the user prescribed maximum threshold can therefore be used as a selection criterion to remove in each graph layer the nodes representing extensions $b_r^>$. Generally, the node removal leads to a much smaller graph structure such that the subsequent shortest-path search is typically faster than the shortest-path search performed in step 203. In order to enforce smooth opening contours and/or a larger opening area a regularization functional is preferentially used to weight all remaining graph edges. The regularization functional may be the regularization value defined in above mentioned equation (2). In order to generate the optimal regular deliverable segment opening, a shortest-path search is applied again to find the best, i.e. less costly, path through the modified layered graph structure.

The fluence map providing unit may be adapted to provide initially several fluence maps for different rotational positions, wherein during the entire optimization procedure the provided fluence maps may be fixed. However, the fluence map providing unit may also be adapted to determine a fluence map for a rotational position, when the optimization procedure is performed for the respective rotational position, such that, after for a certain rotational position optimized segment openings have been determined, the fluence map providing unit provides a fluence map for optimizing the segment openings for a next rotational position.

The device and method for determining illumination distributions to be directed to a target region for performing IMRT described above with reference to FIGS. 1 to 9 can improve the IMRT plan quality, because by definition all generated segments and thus the corresponding illumination distributions are always deliverable. Moreover, the device and method allow for an application of regularization to yield openings with smooth contours or larger areas. The described device for determining the illumination distributions is preferentially adapted to use the fluence-based functional gradient with respect to the segment weights to guide the optimizer towards the minimum as described above.

Although in above described embodiments a multileaf collimator has been used for generating the illumination distributions, in other embodiments also other means, in particular, other collimators, can be used to generate the illumination distributions. For instance, a collimator can be used generating a single illumination line, i.e. a substantially one dimensional line, with variable length, which can be oriented substantially perpendicular to the rotational axis of a rotational movement of the radiation device and which may be moved in the direction of the rotational axis for providing the extensions of the illumination distribution along the parallel lines.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the provision of the ideal fluence map, in particular, the determination of the ideal fluence map, the provision of the layered graph structure, in particular, the determination of the layered graph structure, the determination of the extensions $b_r$ of an illumination distribution, the determination of the second weights, et cetera performed by one or several units or devices can be performed by any other number of units or devices. For example, steps 101 to 107 can be performed by a single unit or by any other number of units or devices. These procedures and/or the control of the device for determining illumination distributions to be directed to a target region for performing IMRT in accordance with the method for determining illumination distributions to be directed to a target region for performing IMRT can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a device for determining illumination distributions for IMRT. A layered graph structure is used, which considers which extensions of an illumination distribution along a respective line and thus which illumination distributions are realizable, for determining extensions for the illumination distributions. Moreover, second weights defining fluences of the illumination distributions are determined such that a deviation between a provided fluence map and a fluence map formed by a combination of illumination distributions, which are defined by the respective determined extensions and the respective second weight, is minimized. This determination procedure leads to illumination distributions, which very well correspond to the provided fluence map and which are automatically realizable by the radiation device. This leads to an improved IMRT, wherein a post-processing of the determined illumination distributions for ensuring that the determined illumination distributions are really realizable is not necessarily required.

The invention claimed is:

1. A device for determining illumination distributions to be directed to a target region for performing intensity modulated radiation therapy, the device comprising:
   a fluence map providing unit for providing a fluence map,
   a layered graph structure providing unit for providing a layered graph structure, wherein the layered graph structure comprises layers with nodes, wherein the nodes of a layer represent realizable extensions of an illumination distribution along a line, which are realizable by a radiation device, wherein the nodes of different layers represent realizable extensions of an illumination distribution along different parallel lines and wherein nodes of adjacent layers are connected by graph edges, to which first weights and regularization values are assigned, wherein the regularization values depend on deviations between the extensions of the illumination distributions represented by the nodes connected by the respective graph edges,
   an extensions determination unit for determining extensions of an illumination distribution along the parallel lines for several illumination distributions, wherein the extensions determination unit is adapted to determine the extensions for an illumination distribution by determining a sequence of nodes connected by the graph edges through the layered graph structure, which optimizes a cost function that depends on a combination of the first weights and the regularization values assigned to the graph edges connecting the nodes of the sequence, thereby determining a contour of the illumination distribution,
   a second weights determination unit for determining second weights defining the fluences of the illumination distributions, for which the extensions have been determined, such that a deviation between the provided fluence map and a combination of the illumination distributions having the determined extensions and the fluences defined by the second weights is minimized.

2. The device as defined in claim 1, wherein the radiation device comprises a combination of a radiation source and a multileaf collimator, wherein the lines, along which the extensions of the illumination distributions are defined, are aligned along the leafs of the multileaf collimator and wherein realizable positions of the leafs of the multileaf collimator define the realizable extensions of the illumination distribution along the respective line.

3. The device as defined in claim 1, wherein the layered graph structure providing unit is adapted to determine a deviation function being indicative of a deviation between the provided fluence map and the combination of illumination distributions having the determined extensions and the fluences defined by the second weights and to determine the first weights depending on the deviation function.

4. The device as defined in claim 3, wherein the layered graph structure providing unit is adapted to determine the first weights depending on gradients of the deviation function.

5. The device as defined in claim 4, wherein the layered graph structure providing unit is adapted to determine a first weight for a graph edge depending on the gradients for the extensions represented by the nodes connected by the graph edge.

6. The device as defined in claim 3, wherein the deviation function is indicative of the sum of squared differences between the provided fluence map and the combination of illumination distributions having the determined extensions and the fluences defined by the second weights.

7. The device as defined in claim 1, wherein the layered graph structure providing unit is adapted to assign an infinite value as a first weight to a graph edge for indicating an impossible transfer from one of the nodes connected by the graph edge to another of the nodes connected by the graph edge, if the combination of extensions of the illumination distribution represented by these nodes is not realizable by the radiation device.

8. The device as defined in claim 1, wherein the layered graph structure providing unit and the extensions determination unit are adapted such that, after the extensions determination unit has determined extensions of an illumination distribution:
   nodes of the layered graph structure are selected based on a selection criterion which depends on the determined extensions,
   regularization values are assigned to the graph edges, and the extensions of the illumination distribution are determined again, wherein only the selected nodes are considered.

9. The device as defined in claim 1, wherein the layered graph structure providing unit, the extensions determination unit and the second weights determination unit are adapted such that the provision of the layered graph structure, the determination of the extensions and the determination of the second weights is repeatedly performed.

10. The device as defined in claim 9, wherein the layered graph structure providing unit is adapted to repeatedly provide the layered graph structure by repeatedly determining the first weights.

11. An apparatus for performing intensity modulated radiation therapy, the apparatus comprising:
   a radiation device for providing illumination distributions to be directed to a target region,
   a device for determining illumination distributions realizable by the radiation device and to be directed to the target region for performing intensity modulated radiation therapy as defined in claim 1, and
   a control unit for controlling the radiation device in accordance with the determined illumination distributions.

12. A method for determining illumination distributions to be directed to a target region for performing intensity modulated radiation therapy, the method comprising:
   providing a fluence map by a fluence map providing unit,
   providing a layered graph structure by a layered graph structure providing unit, wherein the layered graph structure comprises layers with nodes, wherein the nodes of a layer represent realizable extensions of an illumination distribution along a line, which are realizable by a radiation device, wherein the nodes of different layers represent realizable extensions of an illumination distribution along different parallel lines and wherein nodes of adjacent layers are connected by graph edges, to which first weights and regularization values are assigned, wherein the regularization values depend on deviations between the extensions of the illumination distributions represented by the nodes connected by the respective graph edges,
   determining extensions of an illumination distribution along the parallel lines for several illumination distributions by an extensions determination unit, wherein the extensions are determined for an illumination distribution by determining a sequence of nodes connected by the graph edges through the layered graph structure, which optimizes a cost function that depends on a combination of the first weights and the regularization values assigned to the graph edges connecting the nodes of the sequence, thereby determining a contour of the illumination distribution,
   determining second weights defining the fluences of the illumination distributions, for which the extensions have been determined, by a second weights determination unit such that a deviation between the provided fluence map and a combination of the illumination distributions having the determined extensions and the fluences defined by the second weights is minimized.

13. A computer program for determining illumination distributions to be directed to a target region for performing intensity modulated radiation therapy, the computer program comprising non-transitory program code means for causing a device to carry out the steps of the method as defined in claim 12, when the computer program is run on a computer controlling the device.

* * * * *